(12) United States Patent
Lee

(10) Patent No.: US 7,096,731 B1
(45) Date of Patent: Aug. 29, 2006

(54) FINGER GRIPPING FORCE MEASURING DEVICE

(76) Inventor: Mike Chien Ming Lee, 5470 Edgeview Dr., Discovery Bay, CA (US) 94514

( * ) Notice: Subject to any disclaimer, the term of this patent is extended or adjusted under 35 U.S.C. 154(b) by 0 days.

(21) Appl. No.: 11/290,666

(22) Filed: Nov. 29, 2005

(51) Int. Cl.
*A63B 21/02* (2006.01)

(52) U.S. Cl. .................................................. 73/379.03

(58) Field of Classification Search ............... 42/70.01; 81/479; 73/862.21, 379, 379.01, 379.03
See application file for complete search history.

(56) References Cited

U.S. PATENT DOCUMENTS

| | | | |
|---|---|---|---|
| 4,949,729 A | 8/1990 | Haski | 128/774 |
| 6,348,911 B1* | 2/2002 | Rosenberg et al. | 345/161 |
| 6,526,853 B1* | 3/2003 | Jenkins | 81/479 |
| 6,725,728 B1 | 4/2004 | Lee | 73/824 |
| 6,735,897 B1* | 5/2004 | Schmitter et al. | 42/70.01 |

* cited by examiner

*Primary Examiner*—Jewel V. Thompson
(74) *Attorney, Agent, or Firm*—Charles E. Baxley

(57) ABSTRACT

A gripping force measuring device includes a housing having a pressure detecting device and having a handle portion for being held by a user, a trigger attached to the housing and engaged with the pressure detecting device for applying a pressing force against the pressure detecting device when the trigger is forced toward the pressure detecting device. A displayer may be used for displaying the pressing force applied against the pressure detecting device. The trigger includes an arm having a free end extended out of the housing, and a lever is attached to the housing and includes a free end extended out of the housing for allowing the arm to be gripped and forced toward the lever.

11 Claims, 9 Drawing Sheets

FINGER GRIPPING FORCE MEASURING DEVICE

BACKGROUND OF THE INVENTION

1. Field of the Invention

The present invention relates to a gripping force measuring device, and more particularly to a gripping force measuring device for effectively or accurately measuring the gripping force of the users.

2. Description of the Prior Art

Typical gripping force measuring devices comprise an inflatable bladder coupled to or in communication with a pressure transducer which may receive the signals or forces or pressure from the inflatable bladder to calculate or to determine the pressure or the pressure change of the inflatable bladder and thus to obtain the gripping force or gripping rate of the users.

For example, U.S. Pat. No. 4,949,729 to Haski discloses one of the typical gripping rate measuring devices also comprising an inflatable bladder for being held and grasped or gripped by the users, and coupled to a pressure transducer which may receive and calculate the signals or forces or pressure from the inflatable bladder into the pressure or the pressure change of the inflatable bladder or into the gripping force or gripping rate of the users. However, the users may not effectively or suitably grasp or grip the inflatable bladder with their fingers when holding the inflatable bladder.

U.S. Pat. No. 6,725,728 to Lee, the present inventor and applicant, who is the person who first create the finger gripping rate measuring device which comprises an inflatable bladder for being held and grasped or gripped by the users, and a pressing device is further provided and engaged onto the inflatable bladder and includes a pair of opposite flaps for being suitably grasped or gripped by the users. However, the flaps may only be used to detect or to measure the gripping force applied by the thumb and the forefinger, but the flaps may not be suitably used to detect or to measure the gripping force applied by the four fingers of the users. It is to be noted that no testing or measuring device has been developed and available from the market before, and the present inventor and applicant is the person who first create the finger gripping rate measuring device which has been filed and issued in Taiwan, Mainland China, U.S.A.

The present invention has arisen to mitigate and/or obviate the afore-described disadvantages of the conventional gripping force measuring devices.

SUMMARY OF THE INVENTION

The primary objective of the present invention is to provide a gripping force measuring device including a pivotal trigger for being suitably grasped or gripped toward a handle portion by the users to effectively or accurately detect or measure the gripping force of the users.

In accordance with one aspect of the invention, there is provided a gripping force measuring device comprising a housing including a pressure detecting device disposed therein and including a handle portion for being held by a user, a trigger attached to the housing and engaged with the pressure detecting device for applying a pressing force against the pressure detecting device when the trigger is forced toward the pressure detecting device, and a displayer for displaying the pressing force applied against the pressure detecting device.

The displayer is preferably a liquid crystal displayer. The trigger includes an actuator extended therefrom for engaging with the pressure detecting device and for applying the pressing force against the pressure detecting device. The trigger includes an arm extended therefrom and having the actuator extended therefrom. The housing includes a thermometer attached thereto.

The trigger includes an arm having a free end extended out of the housing, and a lever is attached to the housing and includes a free end extended out of the housing and arranged for allowing the arm to be gripped and forced toward the lever. The housing includes a plate disposed therein and preferably having the lever extended therefrom.

The housing includes a compartment formed therein for receiving and anchoring the plate therein. The housing includes at least one jut extended therein for defining the compartment thereof. The displayer is attached to the plate. The arm includes an orifice formed therein and located close to the free end thereof, the lever includes an aperture formed therein and located close to the free end thereof for receiving finger tips of the user.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
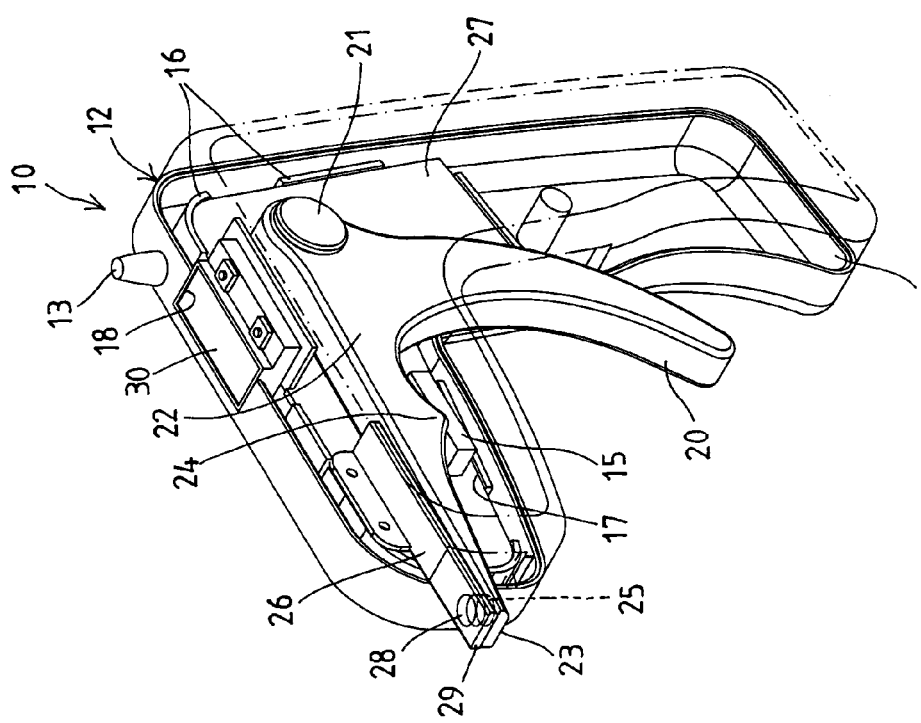
FIG. 1 is a perspective view of a gripping force measuring device in accordance with the present invention, in which one half of the gripping force measuring device has been cut off for showing an inner structure thereof.
Figure 2:
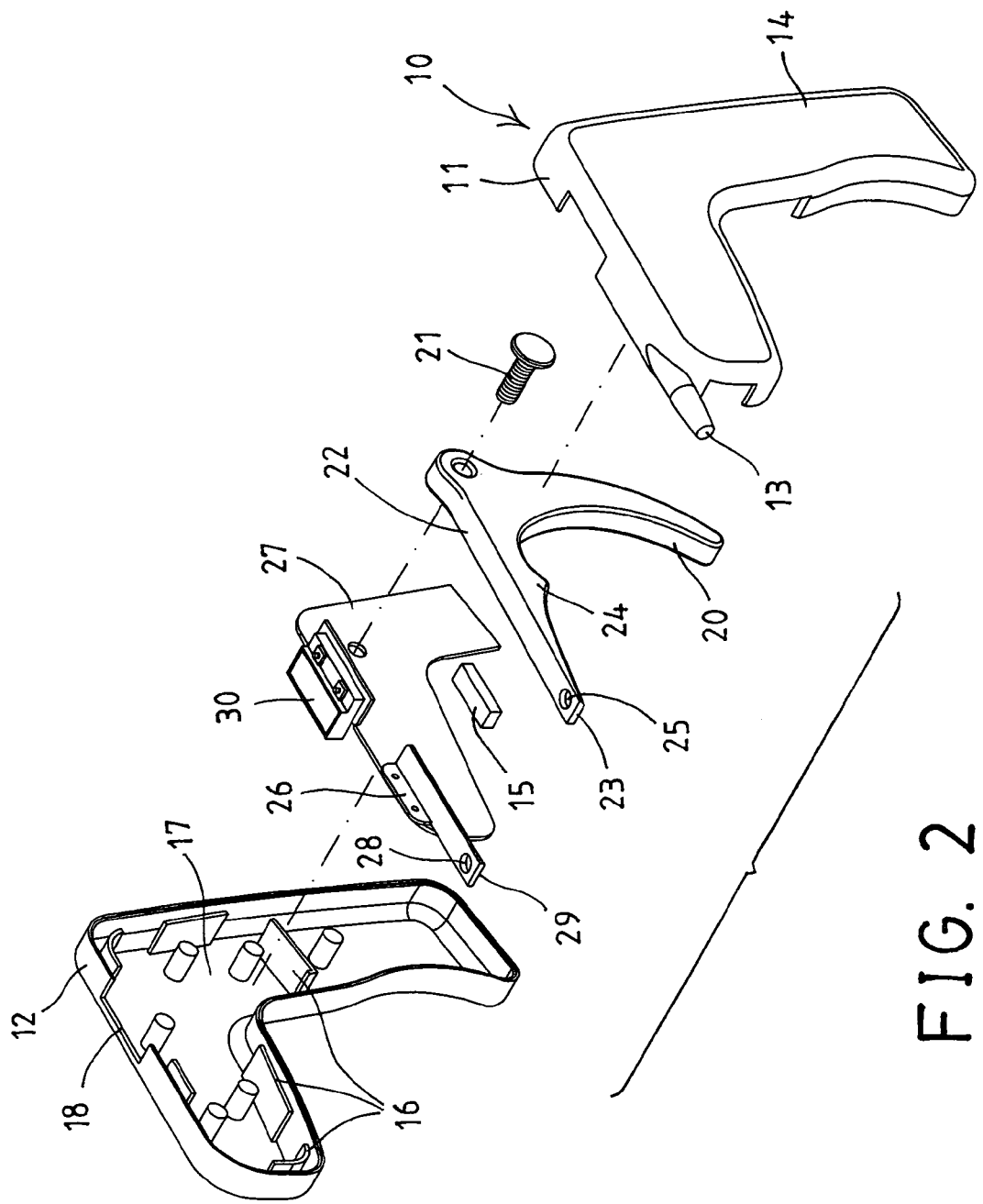
FIG. 2 is an exploded view of the gripping force measuring device.
Figure 3:
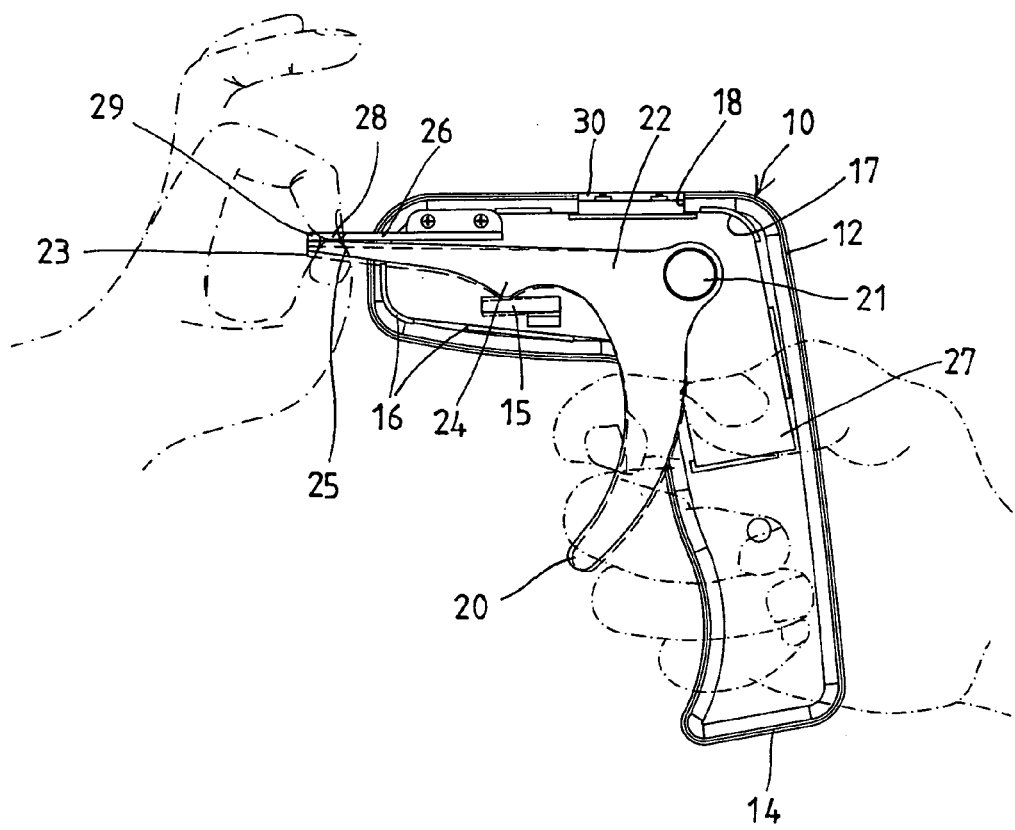
FIG. 3 is a plan schematic view of the gripping force measuring device, in which one half of the gripping force measuring device has also been cut off for showing an inner structure thereof.

Referring to the drawings, and initially to FIGS. 1–3, a gripping force measuring device in accordance with the present invention comprises a body or housing 10 including such as two housing members 11, 12 secured together with such as fasteners or latches (not shown), adhesive materials, or by welding processes, and including a thermometer 13 attached thereto, such as attached to the front portion thereof (FIGS. 2, 5, 6) or attached to the upper portion thereof (FIG. 1) for detecting the temperature of the environment, and including a handle portion 14 for being suitably grasped or held by the users.

A pressure transducer or pressure detecting device 15 is disposed or secured in the housing 10 for being depressed to detect the pressure applied onto the pressure detecting device 15. A hand grip or trigger 20 is pivotally or rotatably attached to the housing 10 with a pivot axle 21, and includes an arm 22 extended therefrom and having one end or free end 23 extended out of the housing 10 (FIGS. 1, 3), and includes a protrusion or actuator 24 extended from the arm 22 for engaging with the pressure detecting device 15 and for applying the pressing or compressing force against the pressure detecting device 15 (FIGS. 1, 3).

It is preferable that the arm 22 includes an orifice 25 formed therein and located closer to the free end 23 thereof. A lever 26 is further provided and secured or attached to the housing 10 directly or indirectly via a plate 27, and also includes an aperture 28 formed therein and located closer to the outer or free end 29 thereof which is also extended out of the housing 10. The housing 10 may include one or more juts 16 extended therein for forming or defining a compartment 17 therein and for receiving and anchoring or securing the plate 27 therein, and thus for allowing the lever 26 to be secured or attached to the housing 10.

Figure 5:
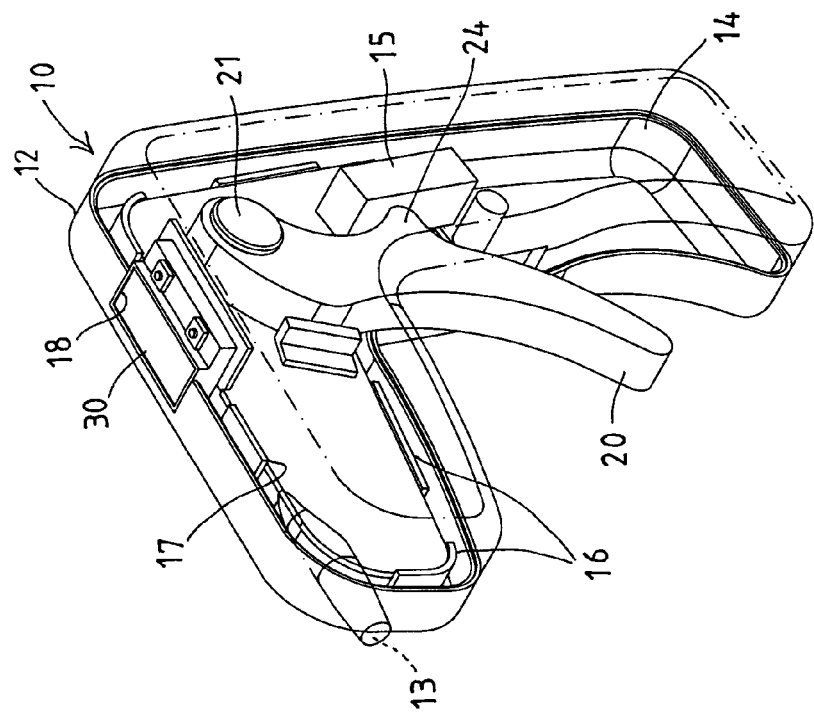
FIG. 5 is a perspective view similar to FIG. 1, illustrating the other arrangement of the gripping force measuring device.
Figure 4:
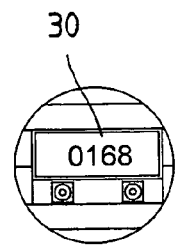
FIG. 4 is a partial top plan schematic view illustrating the displayer of the gripping force measuring device.
Figure 6:
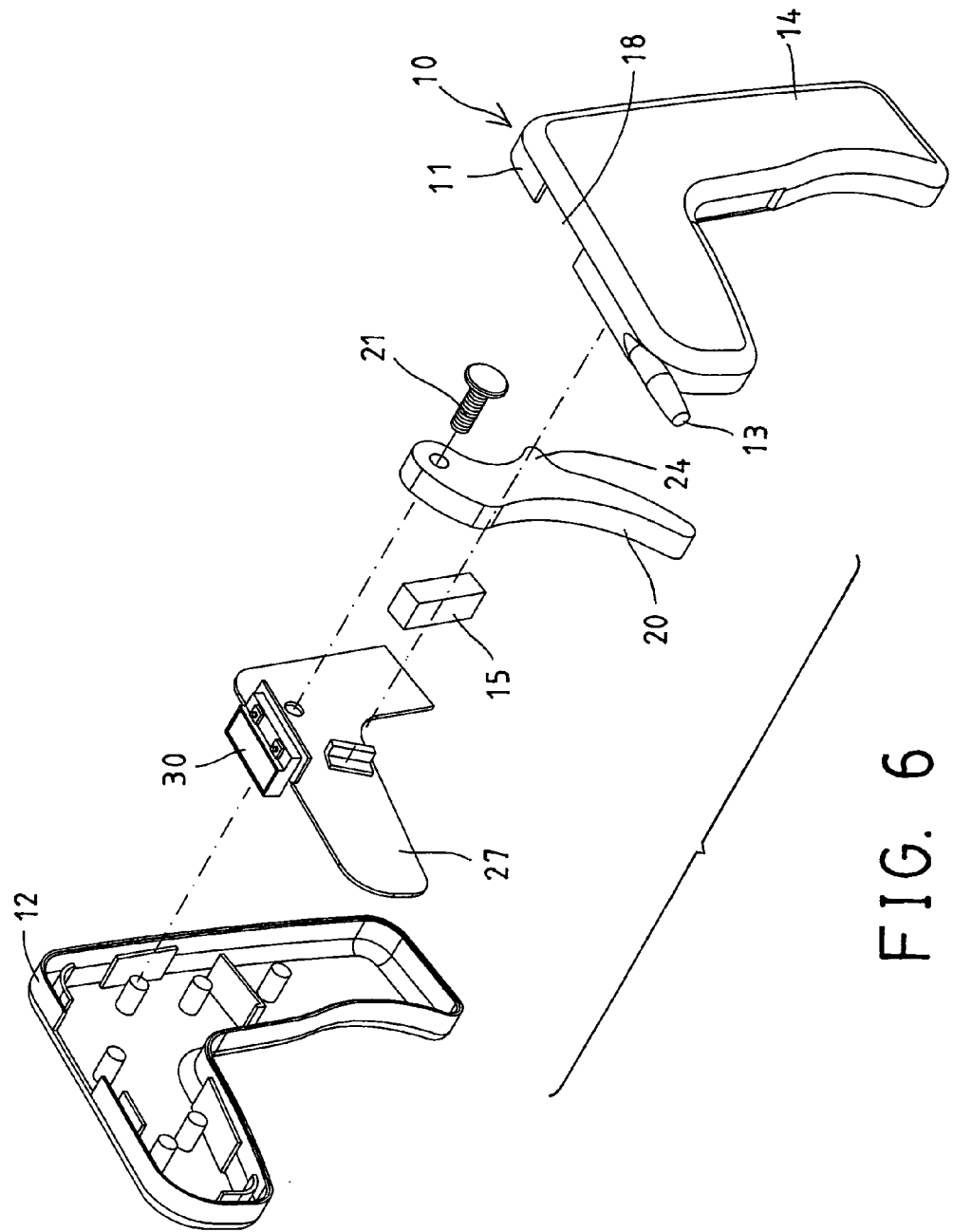
FIG. 6 is an exploded view of the gripping force measuring device as shown in FIG. 5.
Figure 8:
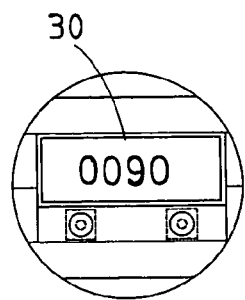
FIG. 8 is a partial top plan schematic view illustrating the displayer of the gripping force measuring device as shown in FIGS. 5–7.

A displayer 30, such as a liquid crystal displayer 30 is further provided and electrically coupled to the pressure detecting device 15 for showing or displaying the pressing or compressing force applied against the pressure detecting device 15, as shown in FIGS. 4 and 8. It is preferable that the housing 10 includes an opening 18 formed therein, such as formed in the upper portion thereof for receiving and anchoring or attaching the displayer 30 which may be attached or secured to the plate 27. Alternatively, as shown in FIGS. 5–7, the protrusion or actuator 24 may also be directly extended from the trigger 20 for engaging with and for forcing against the pressure detecting device 15.

Figure 7:
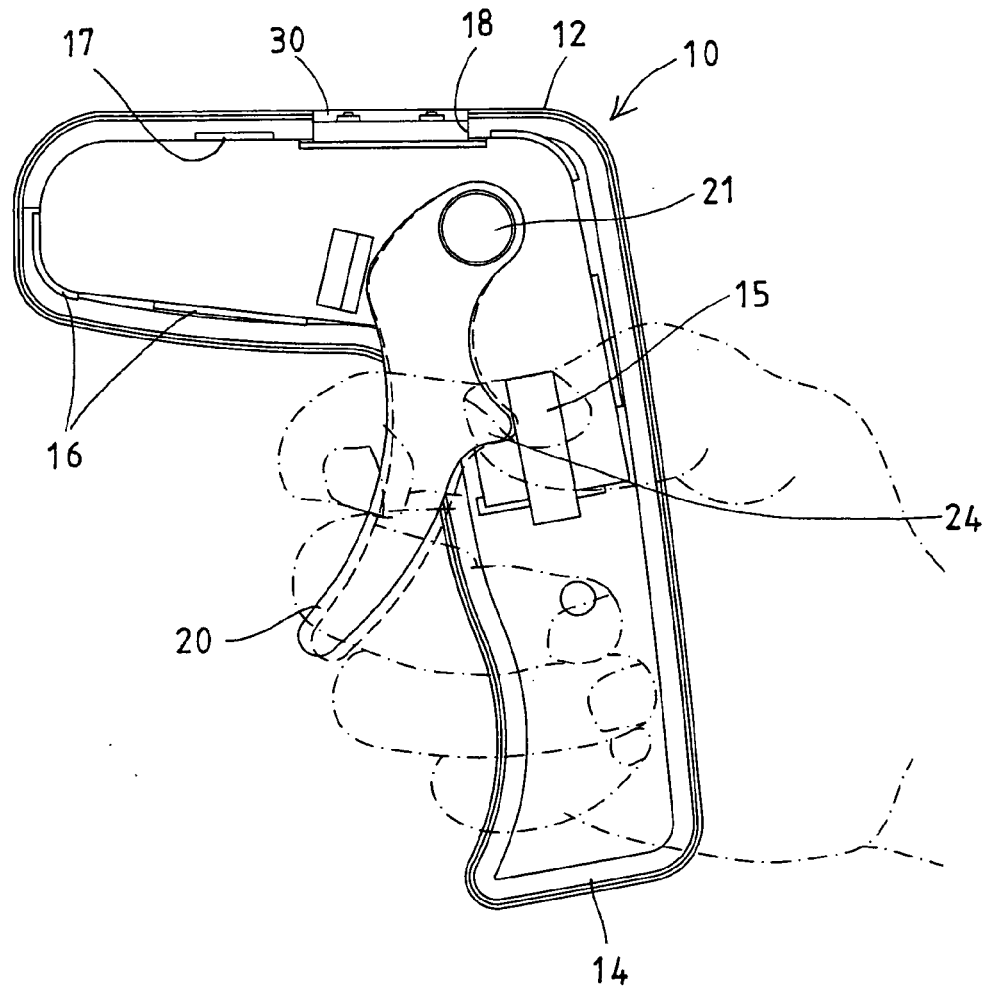
FIG. 7 is a plan schematic view of the gripping force measuring device as shown in FIGS. 5 and 6, in which one half of the gripping force measuring device has also been cut off for showing an inner structure thereof.

In operation, as shown in FIGS. 3 and 7, the user may suitably grasp or hold the handle portion 14 of the housing 10 and may use or engage his two or more fingers with the trigger 20 for allowing the trigger 20 to be effectively or suitably grasped or gripped by the user to effectively or accurately detect or measure the gripping force of the user applied onto or against the pressure detecting device 15, and for allowing the pressing or compressing force applied by the user against the pressure detecting device 15 to be shown or displayed on the displayer 30.

As shown in FIG. 3, alternatively, the user may use his one hand, such as the thumb and the forefinger of his left hand to grasp or grip the arm 22 and the lever 26, and may use his other hand, such as the right hand to grasp or to pull the trigger 20 toward the handle portion 14 of the housing 10 in order to apply the force to force and to separate the arm 22 away from the lever 26. At the moment when or right before the arm 22 is forced and separated from the lever 26, the force of the actuator 24 applied onto the pressure detecting device 15 may be determined as the gripping force of the user applied onto the arm 22 and the lever 26. It is preferable that the displayer 30 is calibrated or set to zero before the trigger 20 is grasped or pulled toward the handle portion 14 of the housing 10. The finger tips of the user may be engaged through the orifice 25 of the arm 22 and the aperture 28 of the lever 26 and may be contacted with each other (FIG. 3).

Figure 9:
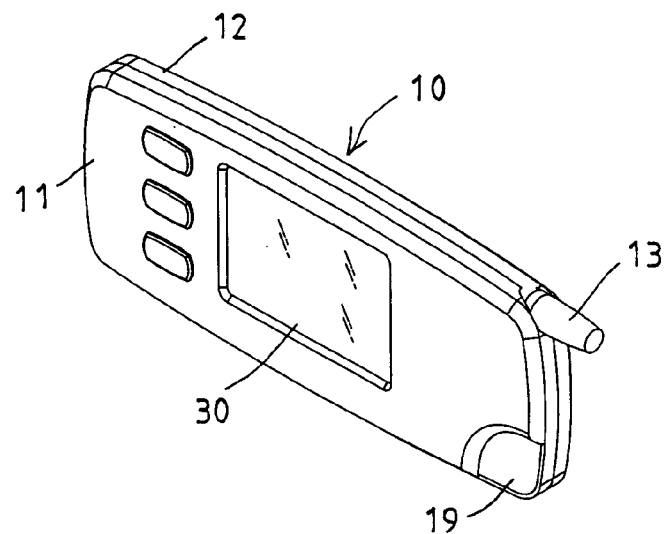
FIG. 9 is a perspective view similar to FIGS. 1 and 5, illustrating the further arrangement of the gripping force measuring device.
Figure 10:
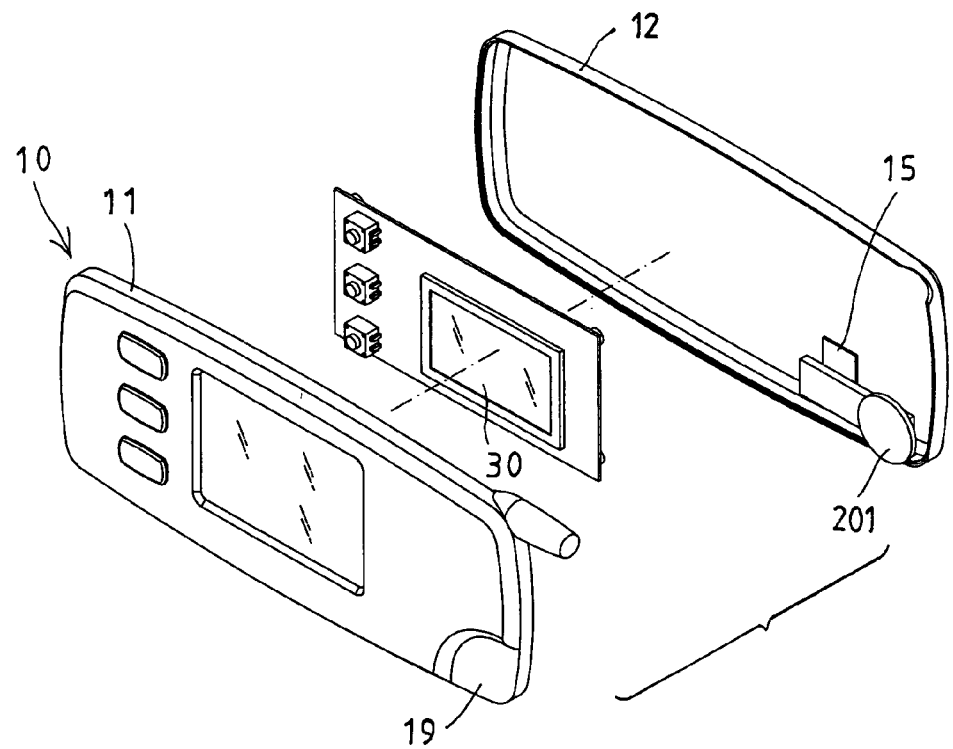
FIG. 10 is an exploded view of the gripping force measuring device as shown in FIG. 9.
Figure 11:
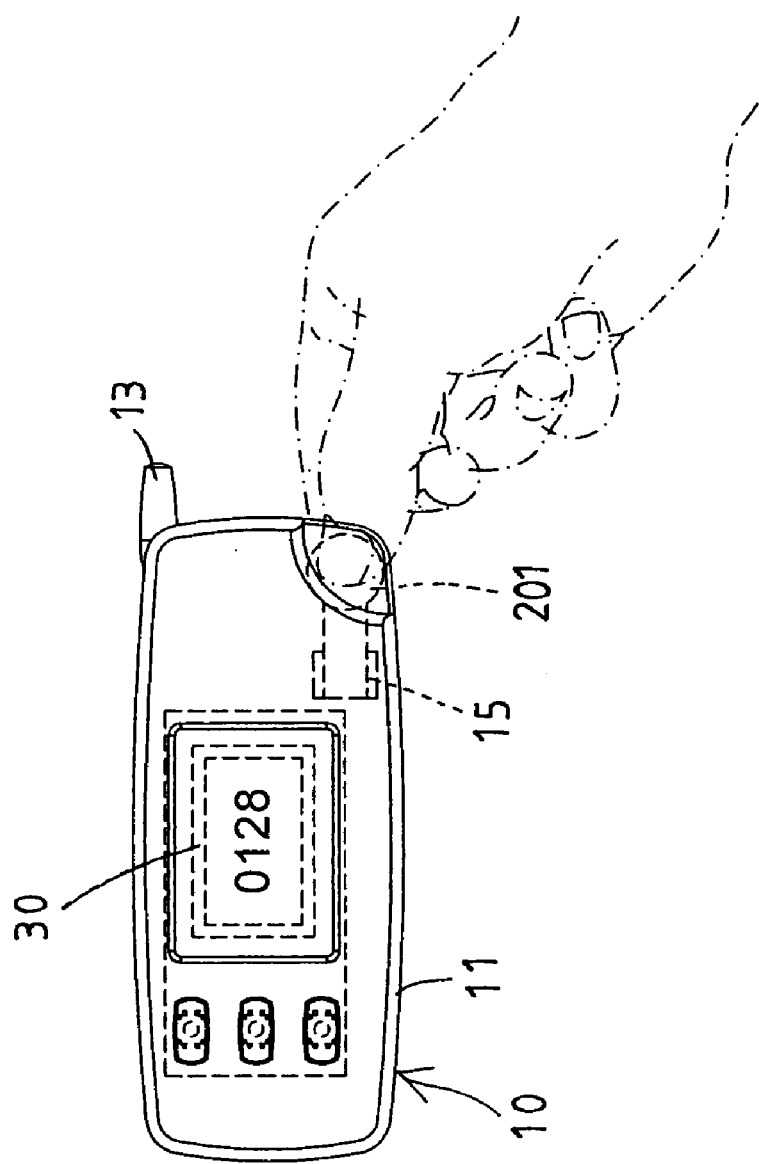
FIG. 11 is a plan schematic view of the gripping force measuring device as shown in FIGS. 9 and 10, illustrating the operation of the gripping force measuring device.
Figure 13:
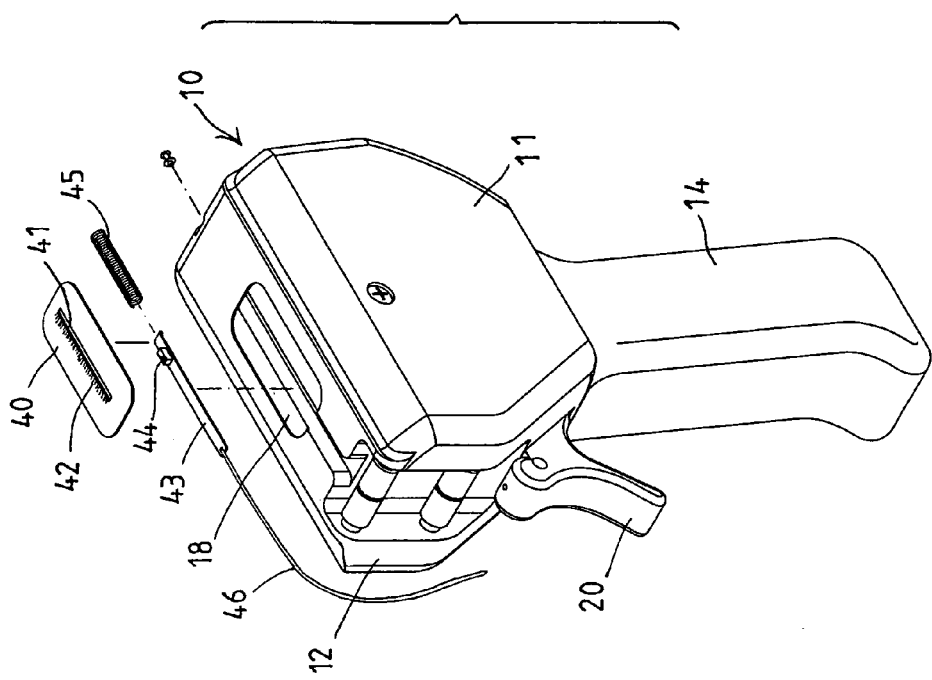
FIG. 13 is a partial exploded view of the gripping force measuring device as shown in FIG. 12.
Figure 12:
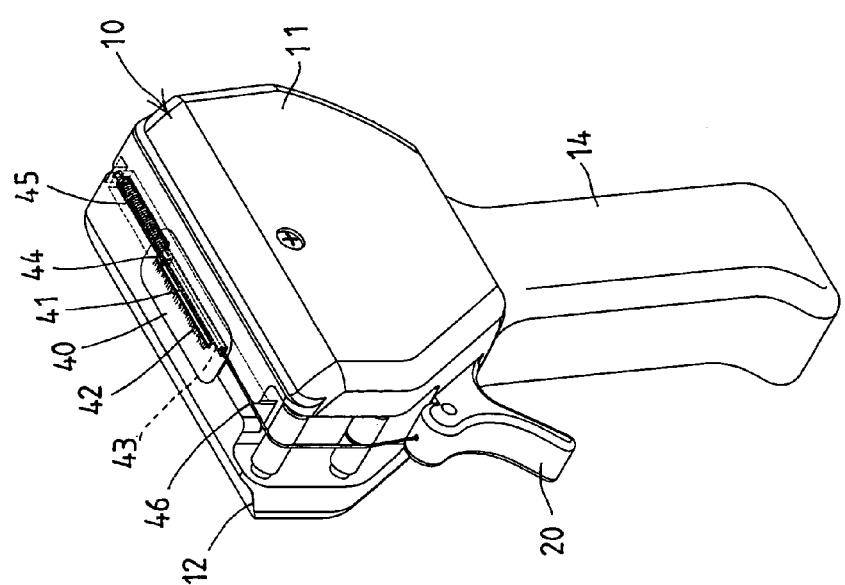
FIG. 12 is a perspective view similar to FIGS. 1, 5 and 9, illustrating the still further arrangement of the gripping force measuring device.
Figure 15:
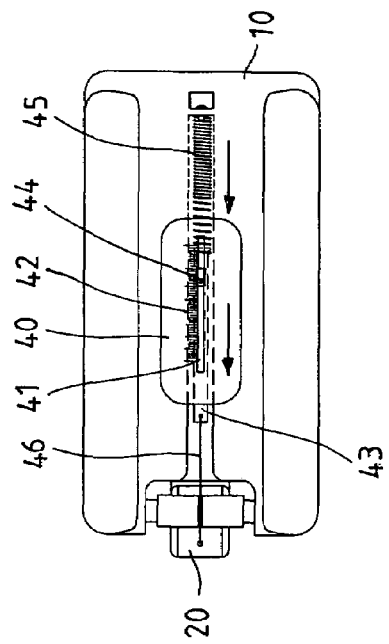
FIG. 15 is a partial top plan schematic view of the gripping force measuring device as shown in FIGS. 12–14.
Figure 14:
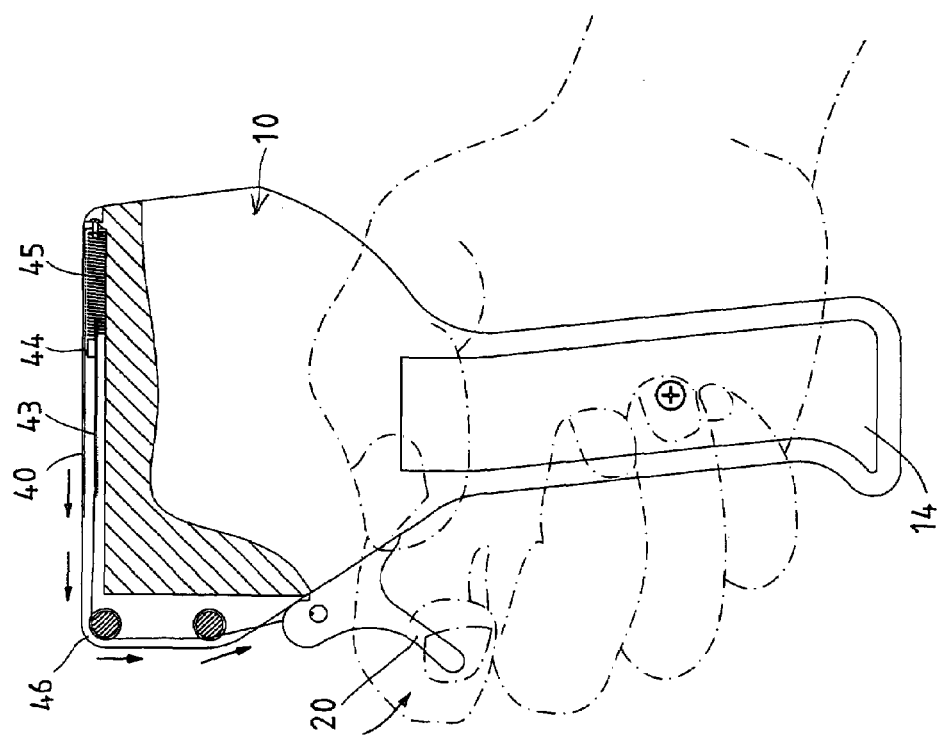
FIG. 14 is a plan schematic view of the gripping force measuring device as shown in FIGS. 12 and 13, in which a portion of the gripping force measuring device has been cut off for showing an inner structure thereof.

As shown in FIGS. 9–11, illustrated is another arrangement of the gripping force measuring device which includes a housing 10 in the form of a mobile or portable phone and also having two housing members 11, 12 secured together and also having the pressure detecting device 15 disposed or secured therein. The trigger 201 is arranged in the form of a pressing knob 201 for engaging with and for forcing against the pressure detecting device 15. The housing 10 includes a depression 19 formed therein and aligned with the pressing knob 201 for guiding the user to grip the trigger 201 and thus the pressure detecting device 15.

As shown in FIGS. 12–15, illustrated is a further arrangement of the gripping force measuring device including a housing 10 having an opening 18 formed in the upper portion thereof for receiving and anchoring or attaching a board 40 which includes a groove 41 formed therein, and a graduation 42 formed and provided along the groove 41 thereof. A bar 43 is slidably received in the housing 10 and located below the groove 41 of the board 40 and includes an indicator 44 extended therefrom and slidably engaged in and moved along the groove 41 of the board 40 for indicating the graduation 42.

A calibrated spring member 45 may be provided and coupled between the bar 43 and the housing 10 for applying a resisting force to the bar 43, and a cable 46 is coupled between the bar 43 and the pivotal trigger 20 for allowing the bar 43 to be slid or moved relative to the housing 10 by the pivotal trigger 20 and against the spring member 45. The indicator 44 of the bar 43 may also be caused to move along the groove 41 of the board 40 (FIGS. 14, 15) and to move relative to the graduation 42 for indicating the graduation 42 corresponding to the pulling or gripping force against the pivotal trigger 20.

It is to be noted that the typical or conventional gripping force measuring devices comprise two flaps for being gripped by the user against the bladder, but fail to provide a pivotal trigger 20 pivotally or rotatably attached to a housing 10 for being grasped or pulled by the user toward the handle portion 14 of the housing 10 in order to determine the gripping force of the user applied onto the handle portion 14 of the housing 10.

Accordingly, the gripping force measuring device in accordance with the present invention includes a pivotal trigger provided for being suitably grasped or gripped by the users to effectively or accurately detect or measure the gripping force of the users.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A finger gripping force measuring device comprising:

a housing including a pressure detecting device disposed therein and including a handle portion for being held by a user, a trigger attached to said housing and engaged with said pressure detecting device for allowing said trigger to be engaged with a finger portion of the user and for applying a pressing force against said pressure detecting device when said trigger is forced toward said pressure detecting device by the finger portion of the user, and a displayer for displaying the pressing force applied against said pressure detecting device.

2. The finger gripping force measuring device as claimed in claim 1, wherein said displayer is a liquid crystal displayer.

3. The finger gripping force measuring device as claimed in claim 1, wherein said trigger includes an actuator extended therefrom for engaging with said pressure detecting device and for applying the pressing force against said pressure detecting device.

4. The finger gripping force measuring device as claimed in claim 3, wherein said trigger includes an arm extended therefrom and having said actuator extended therefrom.

5. The finger gripping force measuring device as claimed in claim 1, wherein said trigger includes an arm having a free end extended out of said housing, and a lever is attached to said housing and includes a free end extended out of said housing and arranged for allowing said arm to be gripped and forced toward said lever.

6. The finger gripping force measuring device as claimed in claim 5, wherein said housing includes a plate disposed therein and having said lever extended therefrom.

7. The finger gripping force measuring device as claimed in claim 6, wherein said housing includes a compartment formed therein for receiving and anchoring said plate therein.

8. The finger gripping force measuring device as claimed in claim 7, wherein said housing includes at least one jut extended therein for defining said compartment thereof.

9. The finger gripping force measuring device as claimed in claim 6, wherein said displayer is attached to said plate.

10. The finger gripping force measuring device as claimed in claim 5, wherein said arm includes an orifice formed therein and located close to said free end thereof, said lever includes an aperture formed therein and located close to said free end thereof for receiving finger tips of the user.

11. The finger gripping force measuring device as claimed in claim 1, wherein said housing includes a thermometer attached thereto.

* * * * *